US009616150B2

(12) United States Patent
Levy et al.

(10) Patent No.: US 9,616,150 B2
(45) Date of Patent: Apr. 11, 2017

(54) BONE HEMOSTASIS METHOD AND MATERIALS

(75) Inventors: Michael Levy, Sherman Oaks, CA (US); Michael Y. Wang, Pasadena, CA (US); Jonathan K. Armstrong, Wells (GB); Timothy C. Fisher, La Crescenta, CA (US)

(73) Assignee: CHILDREN'S HOSPITAL LOS ANGELES, Los Angeles, CA (US)

( * ) Notice: Subject to any disclaimer, the term of this patent is extended or adjusted under 35 U.S.C. 154(b) by 0 days.

(21) Appl. No.: 10/140,015

(22) Filed: Apr. 29, 2002

(65) Prior Publication Data

US 2003/0095945 A1    May 22, 2003

Related U.S. Application Data

(63) Continuation of application No. PCT/US00/29144, filed on Oct. 20, 2000.

(60) Provisional application No. 60/162,347, filed on Oct. 29, 1999.

(51) Int. Cl.
    *A61L 24/04*      (2006.01)
    *C08L 71/02*      (2006.01)

(52) U.S. Cl.
    CPC ............ *A61L 24/04* (2013.01); *A61L 24/043* (2013.01); *A61L 2400/04* (2013.01)

(58) Field of Classification Search
    CPC ......... A61L 24/04; A61L 24/043; C08L 71/02
    USPC ........................................ 424/422, 423, 426
    See application file for complete search history.

(56) References Cited

U.S. PATENT DOCUMENTS

| | | | |
|---|---|---|---|
| 3,122,478 A * | 2/1964 | Lafon .............................. 167/82 |
| 3,465,083 A * | 9/1969 | Bartley et al. ................. 424/342 |
| 4,027,676 A | 6/1977 | Mattei |
| 4,038,388 A * | 7/1977 | Cleaver ......................... 514/153 |
| 4,043,344 A | 8/1977 | Landi et al. |
| 4,047,533 A | 9/1977 | Perciaccante et al. |
| 4,201,216 A | 5/1980 | Mattei |
| 4,407,953 A * | 10/1983 | DeZeeuw et al. ............. 435/145 |
| 4,439,420 A * | 3/1984 | Mattei et al. ............... 424/78.38 |
| 4,440,789 A * | 4/1984 | Mattei et al. .................... 424/78 |
| 4,443,430 A | 4/1984 | Mattei et al. |
| 4,470,416 A | 9/1984 | Kafrawy et al. |
| RE32,208 E * | 7/1986 | Mattei et al. .................... 424/78 |
| 4,716,203 A | 12/1987 | Casey et al. |
| 5,283,067 A * | 2/1994 | Geller et al. .................. 424/489 |
| 5,330,768 A | 7/1994 | Park et al. |
| 5,352,515 A | 10/1994 | Jarrett et al. |
| 5,427,778 A * | 6/1995 | Finkenaur ............ A61K 9/0014 424/78.08 |
| 5,442,016 A | 8/1995 | Jarrett et al. |
| 5,447,966 A | 9/1995 | Hermes et al. |
| 5,454,164 A * | 10/1995 | Yin et al. ........................... 30/41 |
| 5,459,135 A * | 10/1995 | Golub et al. .................. 514/152 |
| 5,503,558 A | 4/1996 | Clokie |
| 5,520,923 A | 5/1996 | Tija et al. |
| 5,641,502 A * | 6/1997 | Skalla et al. .................. 424/426 |
| 5,702,695 A * | 12/1997 | Clokie ....................... 424/78.08 |
| 5,795,584 A | 8/1998 | Totakura et al. |
| 5,817,321 A | 10/1998 | Alakhov et al. |
| 5,840,319 A | 11/1998 | Alakhov et al. |
| 5,840,338 A | 11/1998 | Roos et al. |
| 5,912,228 A * | 6/1999 | Lambert, Jr. .................... 514/12 |
| 5,939,485 A | 8/1999 | Bromberg et al. |
| 6,143,037 A | 11/2000 | Goldstein et al. |
| 6,143,276 A | 11/2000 | Unger |
| 6,296,607 B1 | 10/2001 | Milbocker |
| 6,309,659 B1 * | 10/2001 | Clokie .......................... 424/422 |
| 6,326,018 B1 * | 12/2001 | Gertzman et al. ............ 424/423 |
| 6,331,289 B1 * | 12/2001 | Klaveness et al. ........... 424/9.52 |
| 6,432,381 B2 * | 8/2002 | Liversidge .................... 424/1.29 |
| 6,454,811 B1 | 9/2002 | Sherwood et al. |
| 6,509,028 B2 * | 1/2003 | Williams et al. ............. 424/434 |
| 6,623,748 B2 * | 9/2003 | Clokie .......................... 424/422 |
| 6,673,273 B2 * | 1/2004 | Ba Le et al. .................. 252/511 |
| 6,685,956 B2 | 2/2004 | Chu et al. |
| 6,762,339 B1 | 7/2004 | Klun et al. |
| 2002/0049363 A1 | 4/2002 | Milbocker |
| 2002/0173213 A1 | 11/2002 | Chu et al. |
| 2003/0082235 A1 | 5/2003 | Cohn et al. |
| 2003/0190336 A1 | 10/2003 | Adams et al. |
| 2005/0008609 A1 | 1/2005 | Cohn et al. |
| 2005/0069573 A1 | 3/2005 | Cohn et al. |
| 2005/0165128 A1 | 7/2005 | Cohn et al. |
| 2005/0215748 A1 | 9/2005 | Milbocker |
| 2005/0282997 A1 | 12/2005 | Ward et al. |

FOREIGN PATENT DOCUMENTS

| | | |
|---|---|---|
| EP | 0562612 A1 | 9/1993 |
| EP | 0 884 052 A1 | 12/1998 |
| EP | 1669093 A1 | 6/2006 |
| JP | 03265858 | * 11/1991 |

OTHER PUBLICATIONS

Kabanov et al. ("Pluronic block copolymers as novel polymer therapeutic for drug and gene delivery," in the Journal of Controlled Release 82, Aug. 21, 2002, 189-212).*
1993 SIGMA Catalog, pp. 1539 and 1469.*
Pluronic product, CAS No. 9003-11-6, listed in the BASF catalog, copyright, 1997, p. 34.*
Sato et al. ("Raloxifene (LY139481 HCl) prevents bone loss and reduces serum cholesterol without causing uterine hypertrophy in ovariectomized rats," in J Clin Invest. Jan. 1994; 93(1): 63-69).*
Black et al. ("Raloxifene (LY139481 HCl) Prevents Bone Loss and Reduces Serum Cholesterol without Causing Uterine Hypertrophy in Ovariectomized Rats" in J. Clin. Invest., 1994, pp. 63-69).*
John M. Schmitt et al., *Bone Morphogenetic Proteins: An Update on Basic Biology and Clinical Relevance*, J Orthop Res, 17:269-278 (1999).

(Continued)

*Primary Examiner* — Blessing M Fubara

(74) *Attorney, Agent, or Firm* — Nixon & Vanderhye PC

(57) ABSTRACT

A method for controlling bleeding from bones, comprising the use of copolymers of oxyethylene and oxypropylene or mixtures thereof to cover the bleeding portions of bones. The copolymers are resorbable by the body, not metabolized, simple to prepare, inexpensive, readily available, and do not interfere with the fusion, osteogenesis, and related tissue healing and repair of the affected bones.

26 Claims, 1 Drawing Sheet

(56) References Cited

OTHER PUBLICATIONS

Irving R. Schmolka, *A Review of Block Polymer Surfactants*, J.Amer.Oil.Chemists. Soc. 54:110 (1977).
E. Soiheim, *Growth Factors in Bone*, Int'l Orthop (SICOT) 22:410-416 (1998).
Supplementary European Search Report for European Patent Application No. EP 00 97 2322 dated Nov. 8, 2002, 4 pages.

Schmitt et al. "Bone morphogenetic proteins: An update on basic biology and clinical relevance" J. Orthop. Res. 17:269-278 (1999).
Schmolka "A review of block polymer surfactants" J. American Oil Chem. Soc. 54:110-116 (1977).
Solheim "Growth factors in bone" Int'l Orthop. (SICOT) 22:410-416 (1998).
Wang et al. "A new, pluronic-based, bone hemostatic agent that does not impair osteogenesis" Neurosurgery 49:962-968 (2001).

* cited by examiner

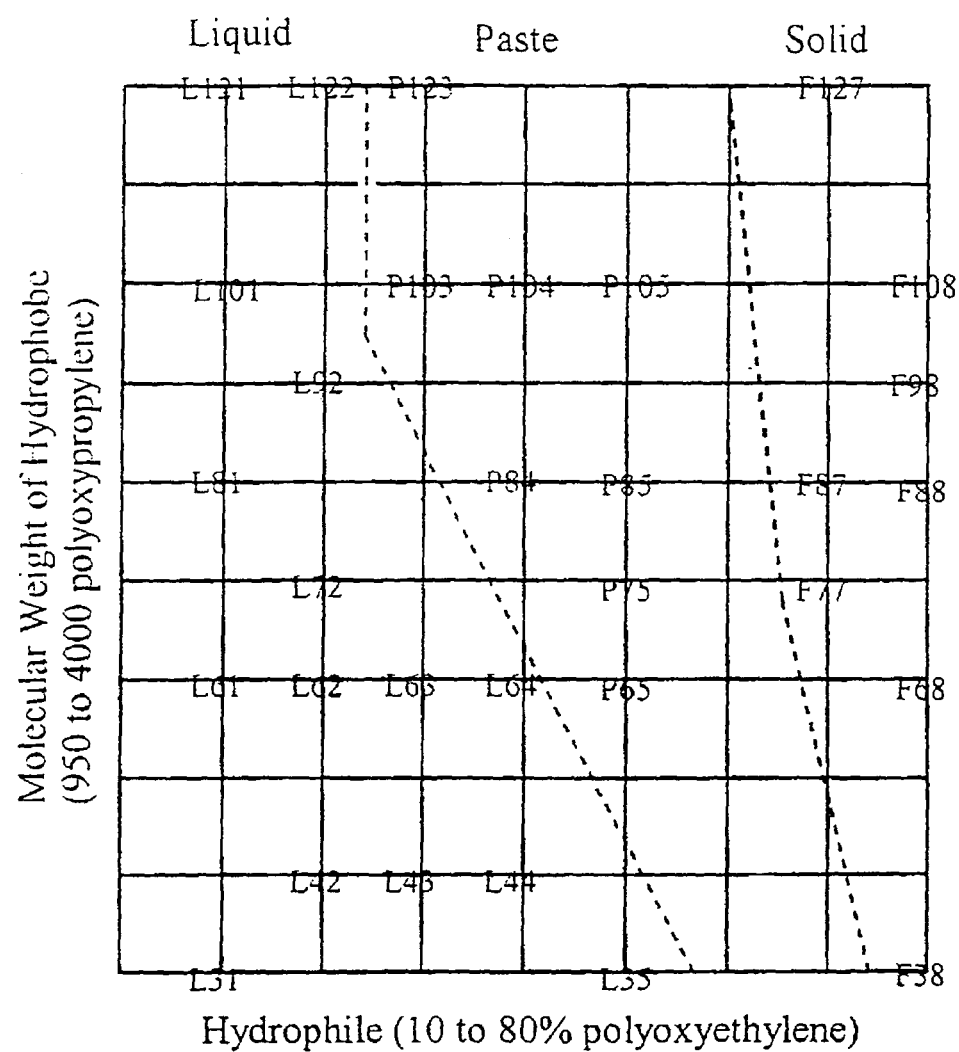

BONE HEMOSTASIS METHOD AND MATERIALS

RELATED APPLICATIONS

This is a continuation application of PCT Patent Application No. PCT/US00/29144 filed on Oct. 20, 2000, designating the United States entitled "Bone Hemostasis Methods and Materials," which claims priority to U.S. Provisional Application No. 60/162,347 filed on Oct. 29, 1999 by Levy et al. with the same title, both incorporated herein by reference in its entirety, including any drawings.

BACKGROUND OF THE INVENTION

Field of the Invention

This invention is in the field of bone hemostasis and involves a method and materials to stop bleeding from bony surfaces via application of copolymers of oxyethylene and oxypropylene during operative procedures or trauma.

Background

During many operative procedures and/or trauma, bones bleed. When such bone bleeding is undesirable and needs to be controlled, cessation of the bleeding, or "hemostasis," has been achieved by several methods in the past. The following methods are presently used to achieve bone hemostasis in surgery requiring fusion of bones:

1. The bones can be permitted to bleed and external drainage can be made for postoperative hematomas;
2. Gel foam or cellulose can be applied locally to the bones;
3. Direct electrocautery can be applied to bleeding bone surfaces;
4. Use of a mechanical barrier such as "bonewax" can be applied to the bones.

Bonewaxes used in surgery today are generally prepared from refined beeswax which has been admixed with other nonabsorbable and water insoluble hydrocarbons and vegetable oils. Certain disadvantages are inherent in these bonewax compositions, such as poor adhesion qualities and brittleness of the wax at room temperatures. In addition, paraffin-based commercial bonenwax is not absorbed by the body and thus remains at the site of the application for long periods of time. As a result, the wax acts as a foreign material tending to make it difficult for the body to fight infection and causing inflammatory reactions that may be introduced into the surrounding tissue. Moreover, the wax interferes with bone regrowth. In addition, bonewax has shown a possible association with increased chromosomal aberrations and teratogenesis in mice. Finally, traditional bonewax has often resulted in the formation of granulomas (a nodular aggregation of inflammatory cells associated with chronic inflammation, which deters proper healing of separated bones and surrounding tissue).

The following have been reported as substitutes for bonewax: gel foam (gelatin) paste; microcrystalline collagen, fibrin-collagen paste, and bioerodible polyorthoester (Alzamer®).

The desirable characteristics in a bone hemostasis agent are: (1) no detrimental effects on bony fusion, (2) non-inflammatory; (3) no increased infection rate; (4) non-toxic; (5) inexpensive; (6) non-teratogenic; (7) effective at achieving bone hemostasis quickly; (8) easily resorbed by the body; (9) not metabolized by the body, which prevents possible toxicity from the compound; (10) water soluble; (11) easily prepared; (12) easy to maintain quality control; (13) maintains chemical stability for long periods of time at room temperature; (14) similar consistency to currently used beeswax. None of the above-listed agents, known agents, or traditional bonewaxes have proven satisfactory in satisfying all these characteristics for a bone hemostasis agent.

The current invention involves the use of copolymers of oxyethylene and oxypropylene. Such copolymers include poloxamers, meroxapols (also known as reverse poloxamers), poloxamines, and PLURADOT® or PLURACOL® (the proprietary name given by the manufacturer BASF; there is no non-proprietary name for PLURADOT®). The principal supplier of these copolymers is BASF, and BASF has given these copolymers the following proprietary names: poloxamers are known as PLURONIC® surfactants; meroxapols are known as PLURONIC® R surfactants; poloxamines are known as TETRONIC® surfactants; and PLURACOL® surfactants. As used throughout this application the terms "copolymers of oxyethylene and oxypropylene" are inclusive of all four of the above listed BASF copolymers. As used throughout this application, the term "PLURONIC®s" is also inclusive of all four of the above-listed BASF copolymers, except as the context otherwise requires, such as in the case of discussing specific examples of specific poloxamers.

PLURONIC® copolymers are organic polymers of varying chain lengths and oxyethylene and oxypropylene ratios. They were developed in the 1950's by BASF and have a number of medical uses. Such PLURONIC®s are currently available at low cost. For a general discussion of PLURONIC®s, see Schmolka. I. J., *Journal of American Oil and Chemical Society. A Review of Block Polymer Surfactants,* 54:110 (1977) (which is incorporated by reference as if fully set forth herein) A general discussion is also included below in the Examples section.

PLURONIC® copolymers are currently used in variety of medical settings, including suture coating, suppositories, intravenous injection to improve blood rheology, and as an additive in artificial blood substitutes. PLURONIC®s have also been utilized to promote osteogenesis when mixed with demineralized bone powder. Although PLURONIC®s have been used as merely additives in some bone hemostasis agents, no bone hemostasis agent has utilized PLURONIC®s as the base material for the agent, as does this invention.

Bone morphogenetic proteins (BMPs) can promote bone regeneration. Schmitt, J. M., Hwang, K., Winn, S. R., Hollinger, J. O., "*Bone Morphogenetic Proteins: An Update on Basic Biology and Clinical Relevance*", J. Orthop. Res., 1999, 17(2), 269-278 (which is incorporated by reference as if fully set forth herein). However, BMPs applied to a site of bone injury will be rapidly resorbed, and therefore will have minimal efficacy, unless they are administered via an appropriate system to maintain sustained delivery of the protein during the course of bone healing. Solheim, E., "*Growth Factors in Bone*", Int. Orthop., 1998, 22(6), 410-416 (which is incorporated by reference as if fully set forth herein). Incorporation of BMPs with bonewax is a very desirable solution as it (a) enhances the therapeutic value of the bonewax; and (b) eliminates the need for a separate sustained delivery system for the BMPs. However, the required property of any material intended as a BMP delivery system is that it should be water soluble or water permeable. Current beeswax based bonewaxes are insoluble and impermeable to water and thus would not fulfill this requirement. However, PLURONIC® copolymers are water soluble and hence would serve as an ideal system to sustain BMP delivery.

SUMMARY OF THE INVENTION

The inventions involve a method and materials for controlling bleeding from bones. The method involves applying a PLURONIC® or mixture of PLURONIC®s over the bleeding site of the bone. The materials used are copolymers of oxyethylene and oxypropylene or mixtures of such copolymers. The invention's advantages over conventional agents currently in use is that it will not retard or prevent bone regrowth and fusion, is water soluble and resorbs into the body, is not metabolized but is excreted whole in the urine and is easily prepared from low cost commercially available materials.

BRIEF DESCRIPTION OF THE DRAWING

FIG. 1 depicts the Basic PLURONIC® Grid.

DETAILED DESCRIPTION OF THE PREFERRED EMBODIMENTS

A bone may be broken or cut during surgery or by trauma. Such a cut or broken bone will then bleed. In order to stop bleeding, the method and materials utilized in this invention involve the application of copolymer of oxyethylene and oxypropylene (PLURONIC®) over the site of the bleeding. The PLURONIC® has the general structure of HO—$(CH_2CH_2O)_A$—$(CH(CH_3)CH_2O)_B$—$(CH_2CH_2O)_A$—H. The PLURONIC® is described generally as a polyoxyethylene-polyoxypropylene-polyoxyethylene triblock copolymer. Thus, there is a hydrophobe (polyoxypropylene) and a hydrophile (polyoxyethylene) present in each PLURONIC® molecule.

In the BASF PLURONIC® code, there are alphabetical and numerical combinations. In BASF's PLURONIC® codes, the alphabetical designation explains the physical form of the product at room temperature: L is for liquids, P is for pastes, and F is for flake (solid) forms. In the numerical designation, the first digit (or the first two digits in a three numeral code) multiplied by 300 indicates the approximate molecular weight of the hydrophobe. The last digit multiplied by 10 indicates the approximate percentage (w/w) of the hydrophile in the PLURONIC®. BASF also makes poloxamers with reverse structures wherein the hydrophilic polyoxyethylene is sandwiched between the hydrophobic polyoxypropylene blocks. This reverse poloxamer or meroxapol is designated as PLURONIC® R by BASF.

Another copolymer which may be used is poloxamine or TETRONIC®, which consists of four chains of polyoxypropylene bounded by four chains of polyoxyethylene. A reverse poloxamine can also be used in which the four chains of ethylene polyoxyethylene are added before the polyoxypropylene. Finally, in PLURADOT® or PLURACOL®, the oxyethylene and oxypropylene are in random order throughout the polymer chain.

As discussed above, PLURONIC® surfactants are currently used in a variety of medical settings. PLURONIC®s range in molecular weight from approximately 1,000 g/mol. to approximately 30,000 g/mol. Low molecular weight PLURONIC®s tend to be liquid in form at room temperature, whereas high molecular weight PLURONIC® s are generally solid at room temperature. Gelling tendencies of PLURONIC®s tend to increase with hydrophile content and with total molecular weight.

In a preferred embodiment of the invention, the PLURONIC® used for the method of stopping bone hemostasis involves a mixture of approximately 10% F88 and 90% P85 where F88 and P85 are PLURONIC® codes utilized by the manufacturer BASF. P85 corresponds to poloxamer code P235 and PLURONIC® code F88 corresponds to poloxamer code P238. This particular combination of P85 and F88 was utilized because it had the consistency of a wax at room temperature. Other combinations of various copolymers of oxyethylene and oxypropylene or the use of a single copolymer of oxyethylene and oxypropylene may also be appropriate for use as a bone hemostasis agent.

The compositions of P85 (P235) and F88 (P238) are as follows:

| PLURONIC® Code | Poloxamer Code | Molecular Mass (g/mol) | Polyoxypropylene Content (g/mol) | Polyoxyethylene Content (g/mol) |
|---|---|---|---|---|
| F85 | P235 | 4650 | 2250 | 2400 |
| F88 | P238 | 11400 | 2250 | 9150 |

The approximate percentages for P85 and F88 useful as a bone hemostasis agent range from about 75%-95% of P85 and about 5% to 25% of F88. The approximate molecular weights of the copolymers useful as bone hemostasis agents range from about 2000 g/mol to about 30,000 g/mol.

The mixture of PLURONIC® P85 and PLURONIC® F88 set forth in the above-described preferred embodiment was specifically blended in order to mimic the physical properties of beeswax-based bonewaxes. In another preferred embodiment of the present invention, a single PLURONIC® copolymer with similar physical properties to currently used beeswax-based bonewaxes would be used. For example, a PLURONIC® with a molecular weight of about 6,000 g/mol, comprising about 60% polyoxyethylene and 40% polyoxypropylene (PLURONIC® code P86), would have comparable physical properties to beeswax-based bonewax.

One method of making the PLURONIC® for bone hemostasis involves placing the PLURONIC® or mixture thereof in a single tube and heating it until it is completely liquid. The PLURONIC® is then placed in a sealed pouch and sterilized by autoclave at 121° C. for 20 minutes. The sterile pouch is then removed from the autoclave at 80° C. and plunged into liquid nitrogen to prevent the formation of crystalline polyoxyethylene.

The PLURONIC® or PLURONIC® mixture is applied to the bleeding portion of a bone via a gloved hand, spatula, syringe or other surgical tool or applicator. A lipstick type applicator which extrudes the copolymer from a cylindrical container by either pushing a bottom plate or rotating the bottom of the applicator may be used. The PLURONIC® or PLURONIC® mixture has the consistency of beeswax and does not crumble or lose its viscosity to any significant degree at either room or body temperature. Like beeswax, the PLURONIC® can be hand molded to fit a bone defect. Alternatively, a less viscous PLURONIC® having reverse thermal gelation properties can be applied by syringe to the affected area of the bone and solidifies upon application or shortly thereafter.

The PLURONIC® or PLURONIC® mixture can stop the bleeding from the bones, yet still allow the two separated ends of the bone to fuse back together. The PLURONIC® or PLURONIC® mixture is water soluble and can be resorbed into the body within approximately 36 hours. In addition, PLURONIC®s are not metabolized but are excreted whole in the urine. In contrast, other hemostasis products often contain chemicals that are metabolized by the body and which may be toxic. PLURONIC®s are non-toxic. The toxicological properties of PLURONIC®s have been investigated since 1952, and they have been shown to have low oral toxicity and low potential for causing irritation or sensitization.

In addition, unlike other bone hemostasis products, PLURONIC®s are very stable at room temperature over long periods of time. Thus, there will be no separation of components or change in form or composition of PLURONIC®s during storage. Also, because the method described in this invention involves either a single PLURONIC® or mixtures of PLURONIC®s, which are simple to prepare and mix, quality control over the final hemostasis agent is improved over previous compounds which are composed of numerous elements.

The PLURONIC®s of the present invention are well suited to be used to administer depot preparations of various medications and drugs. These medications may be mixed with the PLURONIC®s of the present invention and applied to the site of injury. The types of medications that can be used include, but are not limited to: antibiotics, such as aminoglycosides, β-lactam antibiotics, cephalosporins, macrolides, penicillins, tetracyclines, quinolones, and sulfonamides; analgesics, such as acetaminophen, non-steroidal anti-inflammatory agents, salicylates, and narcotics, which may include methadone, morphine, and codeine; chemotherapeutic agents, such as carmustine (BCNU); bone anti-resorption factors, such as risedronate sodium, pamidronate disodium, etidronate disodium, and raloxifene hydrochloride; and bone growth factors, such as calcitonin, TGF Beta (Tumor Growth Factor), and BMP 1 and 2 (bone morphogenic protein). A bone hemostasis agent may further comprise an agent to enhance wound healing and accelerate osteogenesis (e.g., bone morphogenic protein).

In addition, the invention relates to a kit for use in trauma situations, which may contain sterile dressings, sterile PLURONIC® or PLURONIC® mixtures, sterile gloves, adhesive tape, a sterile package for the above-described materials and instructions on how to use the kit.

Nomenclature and the PLURONIC® Surfactant Grid

FIG. 1 is a graphic presentation of the PLURONIC® surfactant series. Plotting molecular weight ranges of the hydrophobe (propylene oxide) against the weight-percent of the hydrophile (ethylene oxide) present in each molecule allows property trends of the product structure to be analyzed on FIG. 1. FIG. 1 also clarifies the use of the letter-number combinations to identify the various products of the PLURONIC® series. The alphabetical designation explains the physical form of the product: 'L' for liquids, 'P' for pastes, 'F' for solid forms. The first digit (two digits in a three-digit number) in the numerical designation, multiplied by 300, indicates the approximate molecular weight of the hydrophobe (vertical axis at the left of FIG. 1). The last digit, when multiplied by 10, indicates the approximate ethylene oxide content in the molecule, read from the horizontal axis. For example, from FIG. 1, we immediately learn that PLURONIC® F 68 is a solid material. The molecular weight of the hydrophobe is approximately 1800 (6×300). The hydrophile represents approximately 80% of the molecule, by weight, (8×10).

The PLURONIC®R Surfactant Grid in FIG. 1 also shows the relationship between the hydrophobe and hydrophile of each product. Again, hydrophobe molecular weight is plotted against weight percent hydrophile. The letter 'R' found in the middle of each designation signifies that this product has a reverse structure compared to the PLURONIC® products, i.e., the ethylene oxide (EP) hydrophile is sandwiched between the propylene oxide (PO) blocks. The numeric designation preceding the 'R', when multiplied by 100, indicates the approximate molecular weight of the PO block. The number following the 'R', when multiplied by 10, indicates the approximate weight percent EO in that product.

| Typical Acute Toxicological Data for Block Copolymers | | | | | |
|---|---|---|---|---|---|
| Block Copolymer Type | Oral $LD_{50}$ | Dermal $LD_{50}$ | Eye Irritation | Skin Irritation | Skin Sensitization |
| PLURONIC ® | 2 to >15 g/kg | >5 g/kg | Non- to Minimal Irritation | Non- to Slight Irritation | Negative to Mild Sensitization |
| PLURONIC ® R | 3 to >10 g/kg | >1 to >10 g/kg | Minimal to Mild Irritation | Minimal to Slight Irritation | Negative |

EXAMPLES

Experiments showing the usefulness of the method have been performed and are described below:

Example 1

General Characteristics of PLURONIC®

The information in Example 1 was obtained from the BASF web site as of Oct. 29, 1999.

FIG. 1 represents the relationship between copolymer structure, physical form and surfactant characteristics by plotting molecular weight ranges of the hydrophobe against the percent of hydrophile in the final molecule. The structure of each grade shown on the grid is defined by the intersection of the hydrophobe molecular weight and the percent hydrophile. FIG. 1 illustrates how gelling tendencies of block copolymers increase with hydrophile-content and with total molecular weight.

The PLURONIC® block copolymers have been analyzed in a variety of subchronic and chronic studies. In general, the studies show that the toxicity of these block copolymers is low and decreases as molecular weight and ethylene oxide content increase. Detailed information for specific products is available on request from BASF.

The effect of PLURONIC® surfactants on aquatic organisms has been evaluated via acute toxicity studies. All the PLURONIC® surfactants tested exhibit low aquatic toxicity. The $LC_{50}/EC_{50}$ values for fish, daphnia and algae range from >100 ppm to >2,000 ppm.

The block copolymers are used in a variety of applications and industries that required federal regulatory authorization. In pharmaceutical and medical applications, the FDA has authorized the use of selected block copolymer surfactants.

Example 2

Rat Femur Non-Union Model

In a group of Sprague Dawley rats, a 3 mm gap was created in femur midshafts by drill, leaving no bony bridge in the gap. The PLURONIC® mixture of 90% P85 and 10% h F88 was applied to the bleeding ends of the bone, and the bleeding stopped. Titanium plating was used to maintain the alignment of the femur. The rats were sacrificed at 11 and 22 days and the femurs examined. Histology (using hemotoxylin and eosin stains) showed that the above described PLURONIC® mixture effectively stopped medullary bone bleeding and did not inhibit new bone growth and fusion (osteogenesis).

Example 3

Rat Femur Defect Model

In a group of Sprague Dawley rats, a 3 mm triangular wedge was removed from the femur midshafts, leaving a bony bridge. The PLURONIC® mixture of 90% P85 and 10% F88 was applied to the bleeding portion of the bony defect. No plating was utilized to maintain bone alignment or structure. The rats were sacrificed at 22 and 44 days and the femurs examined. Histology (using hemotoxylin and eosin stains) showed that the above described PLURONIC® mixture was effective in bone hemostasis and that new bone growth occurred without inhibition by the PLURONIC® mixture. X-rays showed that the PLURONIC® mixture yielded better results than traditional bonewax. X-rays of femurs where the PLURONIC® mixture was applied showed that regrowth of the bones was not inhibited when compared to a defect where no hemostatic agent was used.

Thus, the method and materials of bone hemostasis described in this invention involve the application of a PLURONIC® or PLURONIC® mixture to bleeding bone surfaces, and the PLURONIC® or PLURONIC® mixture does not inhibit bony fusion and osteogenesis. Since certain changes may be made in the proportions of the ingredients composing the bone hemostasis agent and the bone hemostasis method described in this invention, it is intended that all matter and the process described in the above description shall be interpreted as illustrative and not in a limiting sense.

What is claimed is:

1. A non-toxic, hand-moldable, resorbable bone hemostasis composition consisting of (i) a sterile mixture of copolymers consisting of 75-95% poloxamer code P235 and 5-25% poloxamer code P238, wherein said sterile mixture of copolymers has the consistency of wax at room temperature, and (ii) an optional medication to enhance wound healing and accelerate osteogenesis.

2. The non-toxic, hand-moldable, resorbable bone hemostasis composition of claim 1 consisting of said sterile mixture and said medication.

3. The non-toxic, hand-moldable, resorbable bone hemostasis composition of claim 2, wherein said medication to enhance wound healing and accelerate osteogenesis is bone morphogenic protein.

4. A bone hemostasis composition comprising a sterile mixture of copolymers is comprised of 75-95% poloxamer code P235 and 5-25% poloxamer code P238, which is hand moldable at room temperature, in an amount sufficient to stop bleeding when applied to a break or cut in bone.

5. The bone hemostasis composition of claim 4 further comprising a medication.

6. The bone hemostasis composition of claim 5, wherein said medication is selected from the group consisting of antibiotics, analgesics, chemotherapeutic agents, bone anti-resorption factors, bone growth factors, and combinations thereof.

7. The bone hemostasis composition of claim 6, wherein said medication is an antibiotic selected from the group consisting of aminoglycosides, β-lactam antibiotics, cephalosporins, macrolides, penicillines, tetracyclines, quinolones, and sulfonamides.

8. The bone hemostasis composition of claim 6, wherein said medication is an analgesic selected from the group consisting of acetaminophen, non-steroidal anti-inflammatory agents, salicylates, and narcotics.

9. The bone hemostasis composition of claim 6, wherein said medication is carmustine.

10. The bone hemostasis composition of claim 6, wherein said medication is a bone anti-resorption factor selected from the group consisting of risedronate sodium, pamidronate disodium, etidronate disodium, and raloxifene hydrochloride.

11. The bone hemostasis composition of claim 6, wherein said medication is a bone growth factor selected from the group consisting of calcitonin, Tumor Growth Factor Beta, Bone Morphogenic Protein 1, and Bone Morphogenic Protein 2.

12. A method of bone hemostasis comprising: applying to a break or cut in bone such that bleeding is stopped a non-toxic, hand-moldable, resorbable bone hemostasis composition consisting of (i) a sterile mixture of copolymers consisting of 75-95% poloxamer code P235 and 5-25% poloxamer code P238, wherein said sterile mixture of copolymers has the consistency of wax at room temperature, and (ii) an optional medication to enhance wound healing and accelerate osteogenesis.

13. The method of bone hemostasis according to claim 12, wherein said break or cut in bone is due to trauma.

14. The method of bone hemostasis according to claim 12, wherein said break or cut in bone occurs during a surgical procedure.

15. The method of bone hemostasis according to claim 12, wherein a mixture of polyoxyethylene-polyoxypropylene-polyoxyethylene triblock copolymers is applied to said break or cut.

16. The method of bone hemostasis according to claim 12, wherein one polyoxyethylene-polyoxypropylene-polyoxyethylene triblock copolymer is applied to said break or cut.

17. The method of bone hemostasis according to claim 12, wherein said sterile mixture of copolymers is applied with a syringe.

18. A method of bone hemostasis comprising:
   (a) molding a sterile mixture of copolymers to fit a break or cut in bone, the sterile mixture of copolymers is a non-toxic, hand-moldable, resorbable bone hemostasis composition consisting of (i) a sterile mixture of copolymers consisting of 75-95% poloxamer code P235 and 5-25% poloxamer code P238, wherein said sterile mixture of copolymers has the consistency of wax at room temperature, and (ii) an optional medication to enhance wound healing and accelerate osteogenesis, and
   (b) applying said molded copolymer or mixture thereof to said break or cut such that bleeding is stopped.

19. The method of bone hemostasis according to claim 18, wherein said break or cut in bone is due to trauma.

20. The method of bone hemostasis according to claim 18, wherein said break or cut in bone occurs during a surgical procedure.

21. The method of bone hemostasis according to claim 18, wherein a mixture of polyoxyethylene-polyoxypropylene-polyoxyethylene triblock copolymers is molded.

22. The method of bone hemostasis according to claim 18, wherein at least one polyoxyethylene-polyoxypropylene-polyoxyethylene triblock copolymer is molded.

23. A method of bone hemostasis comprising application to a break or cut in bone of a sterile, waxy bone hemostasis composition comprising 75-95% poloxamer code P235 and 5-25% poloxamer code P238, which is hand moldable at room temperature, in an amount sufficient to stop bleeding when applied to a break or cut in bone.

24. The method of bone hemostasis according to claim 23, wherein said bone hemostasis composition consists of a mixture of copolymers of oxyethylene and oxypropylene.

25. The method of bone hemostasis according to claim 23, wherein said bone hemostasis composition is molded to fit the break or cut in bone.

26. The method of bone hemostasis according to claim 23, wherein said bone hemostasis composition is applied with a syringe.

* * * * *